United States Patent
Wätzig et al.

(10) Patent No.: US 10,758,552 B2
(45) Date of Patent: *Sep. 1, 2020

(54) PHARMACEUTICAL COMPOSITION CONTAINING COMBINATIONS OF NICOTINAMIDE AND 5-AMINOSALICYLIC ACID FOR BENEFICIALLY INFLUENCING THE INTESTINAL MICROBIOTA AND/OR TREATING GASTROINTESTINAL INFLAMMATION

(71) Applicant: CONARIS RESEARCH INSTITUTE AG, Kiel (DE)

(72) Inventors: Georg Wätzig, Kiel (DE); Dirk Seegert, Dänischenhagen (DE)

(73) Assignee: CONARIS RESEARCH INSTITUTE AG, Kiel (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/103,406

(22) PCT Filed: Dec. 12, 2014

(86) PCT No.: PCT/EP2014/077637
§ 371 (c)(1),
(2) Date: Jun. 10, 2016

(87) PCT Pub. No.: WO2015/086838
PCT Pub. Date: Jun. 18, 2015

(65) Prior Publication Data
US 2016/0317557 A1   Nov. 3, 2016

(30) Foreign Application Priority Data
Dec. 13, 2013 (EP) .................... 13197261

(51) Int. Cl.
| A61K 31/606 | (2006.01) |
| A61K 9/00 | (2006.01) |
| A61K 31/455 | (2006.01) |
| A61K 45/06 | (2006.01) |
| A61K 9/50 | (2006.01) |

(52) U.S. Cl.
CPC .......... *A61K 31/606* (2013.01); *A61K 9/0031* (2013.01); *A61K 9/0053* (2013.01); *A61K 31/455* (2013.01); *A61K 45/06* (2013.01); *A61K 9/5047* (2013.01)

(58) Field of Classification Search
CPC .................................................. A61K 31/606
USPC .......................................................... 514/161
See application file for complete search history.

(56) References Cited

U.S. PATENT DOCUMENTS

| 6,129,930 | A | 10/2000 | Bova |
| 2005/0063902 | A1 | 3/2005 | Zeligs |
| 2005/0159396 | A1 | 7/2005 | Harty |
| 2006/0264409 | A1 | 11/2006 | Harty |
| 2008/0108684 | A1 | 5/2008 | Matsumoto et al. |
| 2008/0113031 | A1 | 5/2008 | Moodley et al. |
| 2009/0104171 | A1 | 4/2009 | Pardee et al. |
| 2010/0086588 | A1 | 4/2010 | Forbes |
| 2015/0126462 | A1 | 5/2015 | Waetzig et al. |
| 2016/0136147 | A1 | 5/2016 | Højgaard et al. |
| 2016/0317557 | A1 | 11/2016 | Watzig et al. |
| 2017/0027924 | A1 | 2/2017 | Watzig et al. |

FOREIGN PATENT DOCUMENTS

| IT | 2008044099 | * | 4/2008 | ........... A61K 31/606 |
| JP | 2011-121889 A | | 6/2011 | |
| JP | 2012-102054 A | | 5/2012 | |
| WO | WO 97/28801 A1 | | 8/1997 | |
| WO | WO 97/29760 | * | 8/1997 | ........... A61K 31/606 |
| WO | WO 97/29760 A1 | | 8/1997 | |
| WO | WO 98/02148 A2 | | 1/1998 | |
| WO | WO-02/11725 A1 | | 2/2002 | |
| WO | WO-2004/066910 A2 | | 8/2004 | |
| WO | WO 2005/115075 A1 | | 12/2005 | |
| WO | WO 2005/115075 A2 | | 12/2005 | |
| WO | WO 2008/044099 A1 | | 4/2008 | |
| WO | WO 2009/131537 A1 | | 10/2009 | |
| WO | WO 2009/149058 A2 | | 12/2009 | |
| WO | WO 2012/090224 A1 | | 7/2012 | |
| WO | WO 2015/086843 A2 | | 6/2015 | |
| WO | WO-2017/184563 | | 10/2017 | |

OTHER PUBLICATIONS

Jarrett, Clin.Exp.Dermatol. (22, No. 1, 44-45, 1997).*
Andrews, Aliment Pharmacol Ther 2011; 34: 374-383.*
Lawrance Journal of Gastroenterology and Hepatology 26 (2011) 36-43.*
Betterworth, Gastroenterology, vol. 142, No. 5, p. S685, May 2012. (NPL filed Nov. 17, 2016).*
Lu, Letters to the Editor, AJG 96(3), 2001, 932-934 (NPL filed Nov. 17, 2016), Clayton, Eur.J.Pediatr, 19.*
Clayton, Eur.J.Pediatr, 1991, 150, 498-502.*
Gopal Pharmaceutical Research, vol. 24, No. 3, Mar. 2007.*
Tiwari, Drug delivery systems: An updated review, Int J Pharm Investig. Jan.-Mar. 2012; 2(1): 2-11.*
Marriott, Pharmaceutica Compounding and Dispensing, 2005.*
Abdu-Allah, Bulletin of Pharmaceutical Sciences, Assiut University, vol. 28, No. 2, pp. 237-253 (2005).*
Damman, Drug Dev Res 74 : 344-352, 2013.*
Williams, Ther. Adv Gastroenterol (2011) 4(4) 237-248.*

(Continued)

*Primary Examiner* — Nizal S Chandrakumar
(74) *Attorney, Agent, or Firm* — Foley & Lardner LLP (57) ABSTRACT

The present invention relates to a new pharmaceutical composition containing a combination of 5-aminosalicylic acid and nicotinamide or related compounds. The combination is believed to beneficially influence the intestinal microbiota and/or reduce gastrointestinal inflammation. In certain embodiments, the pharmaceutical composition is partially or entirely released into the small intestine or large intestine.

14 Claims, 3 Drawing Sheets

(56) References Cited

OTHER PUBLICATIONS

International Search Report dated Aug. 21, 2015 in application No. PCT/EP2014/077637.
European Search Report dated Feb. 19, 2014 in application No. EP 13 19 7261.
U.S. Appl. No. 62/324,415, filed Apr. 19, 2016, Liang et al.
U.S. Appl. No. 62/324,416, filed Apr. 19, 2016, Liang et al.
International Search Report dated Jun. 19, 2015 in application No. PCT/EP2014/077656 (corresponding to WO 2015/086843).
International Search Report dated Jul. 16, 2013 in application No. PCT/EP2013/062363 (corresponding to US 2015/0126462).
Office Action dated May 6, 2016 in U.S. Appl. No. 14/407,780 (US 2015/0126462).
Hashimoto et al., "ACE2 links amino acid malnutrition to microbial ecology and intestinal inflammation," Nature, vol. 487, pp. 477-481, Jul. 26, 2012.
AbbVie Inc., "NIASPAN®," Highlights of Prescribing Information, Mar. 1, 2013, retrieved from the Internet: http://www.rxabbvie.com/pdf/niapsan.pdf.
Caesar et al., "Effects of gut microbiota on obesity and atherosclerosis via modulation of inflammation and lipid metabolism," Journal of Internal Medicine, vol. 268, No. 4, pp. 320-328, Oct. 2010.
Bettenworth et al., "Nicotinamide Ameliorates the Course of Citrobacter Rodentium-Induced Colitis Through Enhanced Bacterial Killing," Gastroenterology, vol. 142, No. 5, p. S685, May 2012.
Lu et al., "Pellagra in an Immunocompetent Patient with Cytomegalovirus Colitis," Am. J. Gastroenterol., vol. 96, pp. 932-934, 2001.
Penberthy, "Pharmacological Targeting of IDO-Mediated Tolerance for Treating Autoimmune Disease," Curr. Drug Metab., vol. 8, pp. 245-266, 2007.
Sanchez-Fidalgo, "PARP inhibition reduces acute chronic inflammation in rats," Eur. J. Pharmacol., vol. 563, pp. 216-223, 2007.
Filippi et al., "Nutritional Deficiencies in Patients with Crohn's Disease in Remission," Inflamm. Bowel Disease, vol. 12, pp. 185-191, 2006.
Glenn et al., "Synthesis and Mass Spectrometry of Some Structurally Related Nicotinoids," J. Org. Chem., vol. 43, No. 14, pp. 2860-2870, 1978.
Dominiak et al., "Effects of Nicotine and its Major Metabolites on Blood Pressure in Anaesthetized Rats," Klin. Wochenschr., vol. 63, pp. 90-92, 1985.
Clayton et al., "Pellagra with colitis due to a defect in tryptophan metabolism," Eur. J. Pediatr., vol. 150, pp. 498-502, 1991.
Osman et al., "Bifidobacterium infantis strains with and without a combination of Oligofructose and Inulin (OFI) attenuate inflammation in DSS-induced colitis in rats," BMC Gastroenterology, vol. 6, No. 31, doi: 10.1186/1471-230X/6/31, Oct. 28, 2006.
Mazmanian et al., "A microbial symbiosis factor prevents intestinal inflammatory disease," Nature, vol. 453, pp. 620-625, May 29, 2008.
Segal et al., "Rectal manifestations of pellagra," Intl. Journal of Colorectal Disease, vol. 1, pp. 238-243, 1986.
Frank et al., "Molecular-phylogenetic characterization of microbial community imbalances in human inflammatory bowel diseases," PNAS, vol. 103, No. 34, pp. 13780-13785, Aug. 21, 2007.
Written Opinion issued in co-pending Singapore Patent Application No. 11201604759U, dated Jul. 3, 2017.
Abdu-Allah, et al., "Synthesis of Trigonelline and Nicotinamide Linked Prodrugs of 5-aminosalicylic acid (5-ASA) with Analgesic and Anti-Inflammatory Effects," *Bulletin of Pharmaceutical Sciences, Assiut University*, vol. 28, No. 2, pp. 237-253 (2005).
Benowitz et al., "Nicotine Chemistry, Metabolism, Kinetics and Biomarkers," Handbook Exp. Pharmacol., vol. 192, pp. 29-60, Oct. 2009.
Office Action issued in U.S. Appl. No. 15/103,406, dated Aug. 31, 2017 (US 2016/0317557).
"Functions of Vitamin B3," Common Knowledge of Nutrition 1-17 Jan. 1, 2000 http://www.dharmazen.org/X1Chinese/D32Health/H208VitB3.htm [Sections 1 and 6].
International Search Report dated Jun. 19, 2015 in application No. PCT/EP2014/077646.
Kim et al., "L-Tryptophan exhibits therapeutic function in a porcine model of dextran sodium sulfate (DSS)-induced colitis," Journ. Of Nutritional Biochemistry, vol. 21, pp. 468-475 (2010).
Nainggolan, "Niacin/Laropiprant Products to Be Suspended Worldwide," Medscape Medical News, http://www.medscape.com/viewarticle/777519_print, Jan. 2013, retrieved Apr. 9, 2017.
Norwich Pharmaceuticals, Inc., "NIASPAN Prescribing information," Mar. 2013, retrieved from the Internet: http://www.rxabbvie.com/pdf/niaspan.pdf.
Office Action dated Apr. 21, 2017 in U.S. Appl. No. 14/407,780 (US 2015-0126462).
Office Action dated Nov. 10, 2016 in U.S. Appl. No. 14/407,780 (US 2015-0126462).
Office Action dated Aug. 30, 2017 in U.S. Appl. No. 15/103,410 (US 2017-0027924).
Sanyal et al., "Niacin and Laropiprant," Drugs of Today, vol. 46, No. 6, pp. 371-378, Jun. 2010.
Bays et al., "Safety of Niacin and Simvastatin Combination Therapy," The American Journal of Cardiology, vol. 101, Issue 8, Supplement, pp. S3-S8 (2008).
Cheng et al., "Antagonism of the prostaglandin D2 receptor 1 suppresses nicotinic acid-induced vasodilation in mice and humans," PNAS, vol. 103, No. 17, pp. 6682-6687 (Apr. 2006).
Fangmann et al., "Targeted Microbiome Intervention by Microencapsulated Delayed-Release Niacin Beneficially Affects Insulin Sensitivity in Humans," Diabetes Care, vol. 41, pp. 398-405 (Mar. 2018).
Lai et al., "Suppression of Niacin-induced Vasodilation with an Antagonist to Prostaglandin d2 Receptor Subtype 1," Clinical Pharmacology & Therapeutics, vol. 81. No. 6, pp. 849-857 (Jun. 2007).
MYVMC, "Gastrointestinal system anatomy," available on the Internet <URL: https://www.myvmc.com/anatomy/gastrointestinal-system/> (2006).
Oberwittler et al., "Clinical evidence for use of acetyl salicylic acid in control of flushing related to nicotinic acid treatment," The International Journal of Clinical Practice, vol. 60, Issue 6, pp. 707-715 (Jun. 2006).
Office Action dated Oct. 31, 2018 in U.S. Appl. No. 15/103,410 (US 2017/0027924).
Schacht et al., "Polymers for colon specific drug delivery," Journal of Controlled Release, vol. 36, pp. 327-338 (1996).
Notice of Reasons for Rejection dated Mar. 27, 2018 in Japanese Application No. 2015-516627.
Office Action dated Mar. 22, 2018 in U.S. Appl. No. 15/103,410 (US 2017-0027924).
Office Action dated Feb. 7, 2018 in U.S. Appl. No. 14/407,780 (US 2015-0126462).
Wan et al., "Advances in the research of niacin deficiency," J. Pract. Dermatolol., vol. 4, No. 4, pp. 219-222, Dec. 2011.
Office Action dated Aug. 27, 2018 in U.S. Appl. No. 14/407,780 (US 2015-0126462).
Notice of Allowance dated May 20, 2019 in U.S. Appl. No. 14/407,780 (US 2015-0126462).
Office Action dated May 16, 2019 in U.S. Appl. No. 15/103,410 (US 2017-0027924).
Perrie et al., "Controlling Drug Delivery," FASTtrack Pharmaceutics: Drug Delivery and Targeting, second edition, chapter 1 (2012).
Office Action dated Nov. 29, 2019 in U.S. Appl. No. 15/103,410 (US 2017-0027924).

* cited by examiner

PHARMACEUTICAL COMPOSITION CONTAINING COMBINATIONS OF NICOTINAMIDE AND 5-AMINOSALICYLIC ACID FOR BENEFICIALLY INFLUENCING THE INTESTINAL MICROBIOTA AND/OR TREATING GASTROINTESTINAL INFLAMMATION

FIELD OF THE INVENTION

The present invention relates to a new pharmaceutical composition and treatment regimen containing combinations of nicotinamide or related compounds and 5-aminosalicylic acid (5-ASA) or related compounds. These combinations are believed to beneficially influence the intestinal microbiota. The pharmaceutical composition can be specifically released (e.g., selectively released) into the small intestine and/or large intestine.

BACKGROUND

Many inflammatory diseases of the intestinal wall are caused or influenced by changes in the intestinal microbiota and/or an impaired interaction between the intestinal microbiota and the intestines. Such intestinal inflammations occur in humans, e.g., inflammatory bowel diseases (IBD), such as Crohn's disease or ulcerative colitis, but also in other mammals (e.g., chronic idiopathic colitis in dogs). These diseases are based on complex immunological processes which are not fully understood.

However, changes in, and impaired interactions of, the intestinal microbiota can also be causative factors in a number of other diseases. Examples include atopic diseases, such as atopic eczema, allergic conditions or asthma (see e.g., Bisgaard et al. 2011, J. Allergy Clin. Immunol. 128: 646; Iebba et al. 2011, Dig. Dis. 29:531; Abrahamsson et al. 2012, J. Allergy Clin. Immunol. 129:434; Candela et al. 2012, BMC Microbiol. 12:95; Olszak et al. 2012, Science 336:489), as well as metabolic diseases with an inflammatory component, such as arteriosclerosis with resulting coronary heart diseases, adiposity or diabetes (Ott et al. 2006, Circulation 113:929; Koren et al. 2011, PNAS 108 Suppl 1:4592; for reviews see Caesar et al. 2010, J. Intern. Med. 268:320; and Vrise et al. 2010, Diabetologia 53:606).

Although data indicate a pathological or pathophysiological relationship between the intestinal microbiota and various diseases, it has not been understood how to influence the microbiota in a way that would beneficially impact associated diseases.

Nicotinamide (nicotinic acid amide) and the related nicotinic acid (niacin, vitamin B3) have been used for the therapy of niacin deficiency diseases (e.g., pellagra) for decades. It is known that pellagra may be accompanied by intestinal inflammation, which is ameliorated after niacin administration, where the therapeutic principle is restoring the vitamin cofactors needed for normal intestinal cell growth, differentiation and development (Segal et al. 1986, Int. J. Colorectal Dis. 1:238; and Clayton et al. 1991, Eur. J. Pediatr. 150:498).

Formulations containing 5-ASA have also been used for decades in the therapy of IBD, in particular in ulcerative colitis (recently reviewed by: Sonu et al. 2010, Gastroenterol. Clin. North Am. 39:559; Klotz 2012, Arzneimittelforschung/Drug Research 62:53). The mechanism of action of 5-ASA is still unclear, but is considered to be a multifactorial influence on the immune system and inflammatory processes in the inflamed mucosa.

SUMMARY OF THE INVENTION

The object of the present invention is to provide new forms of treatments for the therapy and/or prophylaxis of diseases in humans and animals associated with changes in the intestinal microbiota and/or an impaired interaction between the intestinal microbiota and intestines, where many of these diseases are associated with intestinal inflammation.

According to the invention, the above problem is solved by a pharmaceutical composition or treatment regimen which encompasses combinations of 5-ASA and nicotinamide or another compound described herein, which beneficially influences the intestinal microbiota and their interaction with the intestines. The combination may be present in the same or separate dosage forms, which may be administered simultaneously or sequentially. In preferred embodiments, one or both of nicotinamide and 5-ASA are administered to locally influence the intestinal mucosa and the intestinal microbiota (e.g., the other active substance is optionally administered systemically or only released in part in the lower small intestine and/or colon). For example, the active substance is formulated to be administered selectively in the lower small intestine and/or colon, preferably in the terminal ileum and/or colon, where the intestinal microbiota to be modified are located. Other active substances which convert to nicotinamide in an animal body (e.g., a human body) are also contemplated by the present invention.

Accordingly, pharmaceutical compositions are provided which contain nicotinamide and 5-ASA. These two substances act in combination with one another in an anti-inflammatory and/or beneficial manner. Although the inventors do not wish to be bound by theory, it is believed that the mechanism includes an effect on the microbiota in the small intestine and/or large intestine; this effect may be all or primarily due to the nicotinamide or related compounds. The composition is suitable for oral administration with controlled and/or delayed release of the active ingredient for specific local or topical efficacy in the lower small intestine and/or colon, preferably in the terminal ileum and/or colon. Exemplary conditions treated include therapy or prophylaxis of inflammatory diseases of the small intestine, inflammatory diseases of the large intestine, prophylaxis of colon carcinoma, and therapy or prophylaxis of other diseases which result from changes in the intestinal microbiota and/or an impaired interaction between intestinal microbiota and intestines. The composition is also suitable for the (neo) rectal administration in the colon or pouch for the local and/or topical therapy of inflammatory diseases of the large intestine or pouchitis.

The invention also includes methods of treating one or more of the diseases and conditions described herein with a pharmaceutical composition described herein. In addition, the invention provides the use of a pharmaceutical composition described herein in the manufacture of a medicament for treating one or more of the diseases and conditions described herein.

BRIEF DESCRIPTION OF THE DRAWINGS

FIG. 1 shows histological scores of the colonic mucosa of mice challenged with dextrane sodium sulfate (DSS) colitis and treated with a controlled release granule formulation of NAM mixed in the diet in two doses (30 or 60 mg/kg;

labelled NAM 30 and NAM 60, respectively) without or with a controlled release granule formulation of 5-ASA also mixed in the diet (dose: 150 mg/kg). *, p<0.05 vs. control; **, p<0.01 vs. control.

DETAILED DESCRIPTION

The core of the invention is a pharmaceutical composition or a treatment regimen comprising (i) one, two or more active substance(s) selected from nicotinic acid (NA); nicotinamide (NAM); a compound, e.g., inositol hexanicotinate that converts in the body of an animal (e.g., a human body) into nicotinamide; nicotinamide adenine dinucleotide (NAD); nicotinamide adenine dinucleotide phosphate (NADP); an intermediate in the biosynthesis of NAD or NADP, for beneficially influencing the intestinal microbiota in combination with (ii) 5-ASA or a compound that metabolizes into 5-ASA. A pharmaceutical composition according to the invention preferably is formulated for beneficially influencing the intestinal microbiota. The pharmaceutical dosage forms are optionally designed for a delayed release so that it releases (e.g., partially releases, selectively releases) in the lower small intestine, preferably in the terminal ileum, the colon or both.

As used herein, the "lower small intestine" is the second half of the small intestine and the "terminal ileum" is the second half of the ileum.

It has been previously demonstrated that topical release of nicotinamide in the lower small intestine and/or colon using different controlled- and delayed-release formulations has a surprising anti-inflammatory effect by influencing the intestinal microbiota (the entirety of all microorganisms in the intestines, in particular the bacteria) (PCT/EP2013/062363). The mechanism behind this surprising effect has subsequently been shown to involve nicotinamide-induced changes in the secretion pattern of antimicrobial peptides in the intestines, which supports the maintenance and/or regeneration of the normal, healthy intestinal microbiota (Hashimoto et al. 2012, Nature 487:477). Hashimoto et al. showed that malabsorption of tryptophan in mice leads to a significantly increased severity of colitis induced by the irritant dextran sodium sulfate (DSS). Dietary supplementation of tryptophan or nicotinamide prevented this increase in colitis. Hashimoto et al. demonstrated that the increased susceptibility to severe colitis was due to a changed gut microbiome, which when transplanted to other mice also increased colitis severity in the recipients. The detrimental change in the gut microbiome was found to be due to strongly reduced amounts of certain antimicrobial peptides (AMPs), especially alpha-defensins, whose expression in epithelial cells of the terminal ileum were largely controlled by mTOR signalling induced by tryptophan or nicotinamide.

The inventors have now recognized that a combination of nicotinamide and 5-ASA has a surprisingly superior anti-inflammatory effect, wherein this superior effect is believed to result from an addition of the effects of the two active ingredients and/or a synergistic effect of those ingredients. The altered intestinal microbiota after the administration of a pharmaceutical composition according to the invention have a less inflammation-promoting effect or are anti-inflammatory, thus causing and/or supporting a clear reduction in the symptoms of IBD, such as Crohn's disease or ulcerative colitis, in humans or in other mammals (e.g., chronic idiopathic colitis in dogs).

Thus, as used herein, "beneficially influencing the intestinal microbiota" refers to causing a change in the intestinal microbiota that has a beneficial impact on health, especially on one or more of the diseases and conditions described herein. For example, beneficial impacts are associated with reducing the number of pathogenic bacteria, reducing the ratio of pathogenic bacteria to beneficial bacteria, increasing the diversity of the microbiota, reducing the amount of inflammation that the microbiota induce in the intestines, and partly or completely reverting pathological changes in the enterotype of the microbiota (e.g., enterotypes associated with *Bacteroides, Prevotella* and *Ruminococcus*). Bacteria generally regarded as pathogenic in inflammatory bowel diseases include, for example, Enterobacteriaceae (e.g., *Escherichia coli*) with invasive properties or virulence factors, sulphide-producing *Desulfovibrio* spp. and *Fusobacterium* spp with invasive properties. Bacteria generally regarded as beneficial include species from the genera *Lactobacillus, Bifidobacterium* and *Faecalibacterium*, such as *L. casei, L. plantarum* and *F. prausnitzii*. For a recent overview of the gut microbiota in inflammatory bowel diseases, see Manichanh et al. 2012, Nat. Rev. Gastroenterol. Hepatol. 9:599.

Because chronic intestinal inflammation strongly increases the risk of developing colon carcinoma (for review see e.g., Ullman & Itzkowitz 2011, Gastroenterology 140: 1807), a use of the composition according to the invention is also the prophylaxis of colon carcinoma in the case of a chronic or recurrent intestinal inflammation.

Therapeutic intervention by establishment or re-establishment of a normal gut microbiota or by supplementation of beneficial bacteria has been shown to be efficacious in diverse disease models and in the respective human diseases. For example, Olszak et al. (Science 2012, 336:489) recently demonstrated that the pathological accumulation of invariant natural killer T cells in diseased organs in germ-free murine models of IBD or asthma can be prevented by colonising neonate mice with normal microbiota. In different diseases, studies have demonstrated beneficial effects of certain pre-, pro- or synbiotics. For example, lactobacilli can reduce blood cholesterol levels in obesity, but the mechanism is still not completely clear (reviewed by Caesar et al. 2010, J. Intern. Med. 268:320). In inflammatory bowel diseases, some probiotics like VSL#3 (a mixture of *Bifidobacterium breve, Bifidobacterium longum, Bifidobacterium infantis, Lactobacillus acidophilus, Lactobacillus plantarum, Lactobacillus paracasei, Lactobacillus delbrueckii* ssp. *bulgaricus* and *Streptococcus thermophilus*) have been successfully used in a limited number of clinical studies. It appears that the supplementation of at least several strains of bacteria is usually requisite to provide significant therapeutic benefit. A recent example of spectacular efficacy of a complex bacterial intervention is the successful use of stool transplants against *Clostridium difficile* (van Nood et al. 2013, New Engl. J. Med. 368:407). However, the present invention uses a more subtle approach than a complete microbial ecosystem transplantation by employing the intestine's own signalling mechanims to beneficially influence and, ideally, normalise the endogenous and, thus, endemic gut microbiota.

Because pathological changes in the intestinal microbiota can also play a causal role in numerous other diseases originating from atopic disorders as well as in metabolic diseases with an inflammatory component, the therapy and/or prophylaxis of such diseases is also within the scope of the invention. In particular, the following diseases are examples for such indications:

skin: allergy, atopic eczema, psoriasis;
lung: cystic fibrosis, asthma, COPD;
vessels: coronary heart disease, arteriosclerosis, atherosclerosis;
endocrine system: diabetes, adiposity.

In a preferred embodiment, the invention relates to the specific, topical use of a combination of 5-ASA and nicotinamide (and related active substances) for locally influencing the intestinal mucosa and the intestinal microbiota, intestinal inflammations, and the direct therapy of the intestinal mucosa. It is preferred that at least the NA/NAM-active compound(s) (especially NAM) is used for topical efficiency while in many cases it is even more preferred that both the NA/NAM compound(s) and 5-ASA are used for topical efficiency.

As used herein, the term "topical efficacy" refers to a topical effect, in the pharmacodynamic sense, and thus refers to a local, rather than systemic, target for a medication. Accordingly, local efficacy means a local therapy and/or prophylaxis of an active substance specifically or selectively to a location where, for example, the medication shall deliver its direct therapeutic and/or prophylactic effect and does not or only to a low degree enter the circulatory system, e.g., thereby not causing any or only a low systemic action. In this regard, the topical efficacy of the present invention is also contrasted with enteral (in the digestive tract) and intravascular/intravenous (injected into the circulatory system) administrations. In comparison to compositions aiming at high systemic availability, the topical efficacy of compositions may also be characterized by longer latency times until systemic levels of the active substance(s) increase. Such latency times for topical release can be correlated with intestinal transit times known in the art (see, e.g., Davis et al. 1986, Gut 27:886; Evans et al. 1988, Gut 29:1035; Kararli 1995, Biopharm. Drug Dispos. 16:351; Sutton 2004, Adv. Drug Deliv. Rev. 56:1383). For example, after a variable time for gastric emptying (depending on the dosage form and feeding status and ranging from less than 1 hour to more than 10 hours), small intestinal transit times are rather constant with usually 3-4 hours across formulations and studies (Davis et al. 1986, Gut 27:886). Thus, an exemplary latency time in a fasted patient would be at least 2 hours, at which time a formulation reaches the lower small intestine and systemic levels may start to rise. Particularly, in the context of the present invention, topical efficacy preferably means that blood and/or plasma and/or serum levels of the active substance (e.g., NA/NAM component) and/or metabolites thereof do not exceed levels which are two orders (preferably one order) of magnitude higher than the levels measured in the same person before dosing. Alternatively or additionally, topical efficacy can be expressed in terms of a reduction of the blood and/or plasma and/or serum levels of at least 50%, 60%, 70%, 80%, 90% or even 95% or more relative to the same amount of active agent administered purely (without a formulation) in the same way and under the same conditions.

While it is preferred according to the invention that the pharmaceutical composition comprises both the 5-ASA component and the NA/NAM component within just one preparation, it may be beneficial to have two separate pharamaceutical compositions each comprising just one of the active ingredients (5-ASA component or NAM/NA component) to be administered together under a treatment regimen. It has to be noted that such a set of pharmaceutical compositions (to be administered together under a treatment regimen) is per definition for this application a pharmaceutical composition according to the invention, too.

In this regard, the present invention also comprises combination preparations of the active substances of the present invention, such as a variable dose combination or a fixed dose combination of the 5-ASA component and the NA/NAM component. The combination described herein may be present in the same or separate dosage forms, which may be administered simultaneously or sequentially. Even within the same dosage form, the 5-ASA component and the NA/NAM component may be physically segregated.

As used herein, the term "variable dose combination" refers to a drug/drug combination of two or more active substances whereby each of these substances is applied in the form of a separate pharmaceutical composition, e.g., two single dosage forms, which separate pharmaceutical composition may be administered together by consecutive or subsequent administration regimen. For example, a pharmaceutical composition of 5-ASA in any suitable dosage thereof may be administered together, consecutively or subsequently, with a separate pharmaceutical composition of nicotinamide in any suitable dosage thereof. Thus, variable dosages of one active substance, e.g., of 5-ASA, may be combined with variable dosages of another active substance, e.g., of nicotinamide. These variable dose combinations may use conventionally available pharmaceutical compositions or may be also achieved by customised polypharmacy via compounding.

In contrast to a variable dose combination, a fixed-dose combination is a combination drug which is a formulation including two or more active pharmaceutical ingredients, e.g., active substances, combined in a single dosage form, which is manufactured and distributed in certain respective fixed doses. A fixed-dose combination mostly refers to a mass-produced product having a predetermined combination of drugs (active substances) and respective dosages (as opposed to customised polypharmacy via compounding).

The topical use significantly differs from conventional uses of the active substances, where these substances are absorbed and are supposed to act systemically. On account of their new anti-inflammatory effect and/or their effect modifying the intestinal microbiota, nicotinamide (and the other compounds described herein) are thus suitable as active substances for treating inflammatory diseases of the small intestine and/or large intestine in combination with 5-ASA. Particular conditions include the treatment of intestinal inflammations, the prophylaxis of colon carcinoma, and the therapy or prophylaxis of other diseases that result from changes in the intestinal microbiota and/or an impaired interaction between the intestinal microbiota and the intestines. Preferably, these active substances and combinations are used in a pharmacological formulation that protects the largest possible amount of active substance from being absorbed by the body in the upper small intestine and rather effects a release (e.g., controlled release and/or delayed release) into the lower small intestine and/or colon, preferably the terminal ileum and/or colon, where the intestinal microbiota to be modified are located (e.g., the active substance is selectively released in the lower small intestine and/or colon, preferably in the terminal ileum and/or colon).

In an embodiment, the nicotinamide (or related compound) is administered to locally (topically) influence the intestinal mucosa and the 5-ASA (or related compound) is administered such that all or part releases anywhere in the stomach, small intestine or large intestine (e.g., colon). The 5-ASA can also be formulated to control the release, such as according to known formulations such as ethylcellulose coating (e.g., PENTASA), multi-matrix technology (e.g., LIALDA), and enteric coating (e.g., methacrylic acid polymers and copolymers such as in APRISO, ASACOL, ASACOL HD).

In particular, the combinations described herein are thus suitable for being used in medicaments for the therapy of Crohn's disease, ulcerative colitis, pouchitis, further chronic diseases of the large intestine or inflammations of the large intestine, diversion colitis, infectious enteritis, antibiotic-associated diarrhea such as *C. difficile*-associated diarrhea, infectious colitis, diverticulitis and inflammations which are formed by irradiation, by antibiotics, by chemotherapeutic agents, by pharmaceutical products or by chemicals, as well as for the prophylaxis of colon carcinoma and for the therapy or prophylaxis of other diseases which result from changes in the intestinal microbiota and/or an impaired interaction between intestinal microbiota and intestines.

The claimed substances are equally usable for the therapy or prophylaxis of diseases with similar genesis in both human and other mammals, in particular in domestic and useful animals. Examples of such animals are dogs, cats, horses, camels or cows without objective restriction.

Active substances, i.e., nicotinamide, may be used in any form available on the market, e.g., produced by Merck KgaA.

As NA/NAM component in addition to nicotinic acid or nicotinamide, other related compounds can be used in the invention described herein as active substances. For example, compounds that convert into one of these agents (e.g., by hydrolysis, metabolism) in the human or animal body are suitable, such as nicotinic acid esters (e.g., inositol hexanicotinate). In addition, intermediates in the synthesis of nicotinamide adenine dinucleotide (NAD) or NAD phosphate (NADP), such as N-formylkynurenine, L-kynurenine, 3-hydroxy-L-kynurenine, 3-hydroxyanthranilate, 2-amino-3-carboxymuconate semialdehyde, quinolinate, and beta-nicotinate D-ribonucleotide, can be used. Further examples include NAD and NADP.

As 5-ASA component in addition to 5-ASA, other related compounds can be used in the invention described herein as active substances. For example, compounds that convert into 5-ASA (e.g., by hydrolysis, metabolism) in the human or animal body are suitable, such as the prodrugs sulfasalazine and balsalazide.

Pharmaceutical compositions which contain a combination of 5-ASA and nicotinamide (or one of the other substances described above), can preferably be administered orally (e.g., with a retarded active substance release) or also preferably via a rectal mode of application (e.g., enemas or suppositories). The site of delivery of the active substance, particularly nicotinamide, is preferably the lower portions of the small intestine and/or the colon for inhibiting inflammatory processes, and thus differs fundamentally from modes of applications which—e.g., for the therapy of pellagra with nicotinamide—pursue maximal absorption and metabolism in the organism and thus a systemic effect. In addition, the mode of administration according to the invention and the dosage according to the invention minimise the probability for the occurrence of side effects, for example as described in connection with the systemic administration of larger doses of nicotinamide.

In order to produce orally administered formulations of an active combination having an anti-inflammatory and/or modifying effect on the intestinal microbiota in the terminal ileum and/or in the colon, it is thus advantageous to use controlled and/or delayed modes of release. In contrast to conventional (in some cases also delayed) modes of release for optimum supplementation with nicotinamide, e.g., in the case of pellagra, certain embodiments of the present invention partially or substantially avoid an absorption in the stomach and in the upper portions of the small intestine.

In order to treat Crohn's disease or ulcerative colitis, oral and/or rectal modes (e.g., as enema) of application are suitable. In order to treat pouchitis in the case of ulcerative colitis, the rectal application (e.g., as enema) is preferred. It can also be supported by an oral administration of the oral formulations described above, e.g., delayed releasing preparations. For the symptomatic therapy of any other form of colitis, both the oral and rectal applications can be chosen for the therapeutic modification of the intestinal microbiota. The oral application is preferred for the prophylaxis of the colon carcinoma, in particular in the case of ulcerative colitis, and for the therapy and/or prophylaxis of other diseases which partially or substantially result from changes in the intestinal microbiota and/or an impaired interaction between intestinal microbiota and the intestines.

For oral administration, particular dosage forms that control and/or delay the release of the active substance due to special galenics (so-called controlled release, slow release or delayed release forms) are particularly suitable. Such dosage forms may be simple tablets and also coated tablets, e.g., film tablets or dragees. The tablets are usually round or biconvex. Oblong tablet forms, which allow the tablet to be separated, are also possible. In addition, granules, spheroids, pellets or microcapsules are possible, which are filled in sachets or capsules, where appropriate.

The term "delayed release" relates preferably to a pharmaceutical formulation that releases the active ingredients after a period of delay. In certain embodiments, the delay is sufficient for at least a portion of the active substances in a formulation to release in the lower small intestine (e.g., terminal ileum) and/or colon.

The term "controlled release" refers preferably to a pharmaceutical formulation or component thereof that releases, or delivers, one or more active ingredients over a prolonged period of time (time-dependent release) and/or under certain physiological conditions (e.g., pH-dependent release). In certain embodiments, the period of time or the release according to physiological conditions (e.g., pH) is sufficient for at least a portion of the active substances in a formulation to release in the lower small intestine (e.g., in the terminal ileum) and/or colon.

The retardation and/or delayed release and/or controlled release is advantageously achieved, e.g., by coatings which are resistant to gastric juice and dissolve depending on the pH, by means of microcellulose and/or multi matrix (MMX) technologies, by using different carrier matrices or a combination of these techniques. Examples include film coatings which contain acrylic and/or methacrylate polymers in various mixtures for controlled and/or delayed release. For example, the active substance(s) can be contained in a conventional matrix of microcrystalline cellulose or gelatin or with MMX technology, which is coated with a material, which provides the delayed release of the active substance(s). An active substance can be administered in large-volume capsules (e.g., gelatin capsules having a content of 0.68 ml), which are coated by means of known methods. Suitable coating agents are water-insoluble waxes, such as carnauba wax, and/or polymers, such as poly(meth) acrylates [e.g., the poly(meth)acrylate product portfolio with the trade name Eudragit®, in particular Eudragit® L 30 D-55 (an aqueous dispersion of anionic polymers with methacrylic acid as a functional group), Eudragit® L 100-55 (which contains an anionic copolymer based on methacrylic acid and ethyl acrylate), Eudragit® L 100 or L 12,5 or S 100 or S 12,5 (anionic copolymers based on methacrylic acid and methyl methacrylate), or Eudragit® FS 30 D (an aqueous dispersion of an anionic copolymer based on methyl acrylate, methyl methacrylate and methacrylic acid); Evonik Industries AG, Essen, Germany) and/or water-insoluble celluloses (e.g., methyl cellulose, ethyl cellulose). Where appropriate, water soluble polymers (e.g., polyvinylpyrrolidone), water-soluble celluloses (e.g., hydroxypropylmethyl cellulose or hydroxypropyl cellulose), emulsifiers and stabilisers (e.g., polysorbate 80), polyethylene glycol (PEG), lactose or mannitol can also be contained in the coating material.

For example, a combination of Eudragit® S and L compounds (e.g., Eudragit® L/S 100) effects a controlled release of the active substances according to the invention at pH>6.4, which occurs in the terminal ileum. Further uses of Eudragit® preparations and mixtures thereof (FS, L, S and R compounds) are also conceivable for the packaging of an active substance, and therefore a topical use in selected portions of the entire gastrointestinal tract can be achieved by controlled release at certain pH values. A systematic study of enteric targeting with hydroxypropyl methylcellulose (HPMC) capsules and more recently developed Eudragit® polymers was published by Cole et al. in 2002 (Int. J. Pharm. 231:83).

The pharmaceutical composition can also contain further pharmaceutical excipient substances, such as binders, fillers, glidants, lubricants and flow regulating agents. The compounds according to the invention can be formulated, where appropriate, together with further active substances and with excipients conventional in pharmaceutical compositions, e.g., talcum, gum arabic, lactose, starch, magnesium stearate, cocoa butter, aqueous and non-aqueous carriers, lipid components of animal or vegetable origin, paraffin derivatives, glycols (in particular polyethylene glycol), various plasticizers, dispersants, emulsifiers and/or preservatives.

In order to produce enemas or suppositories for rectal application, preparations of an active substance can be dissolved in a suitable solvent and be further processed into enemas or suppositories according to known pharmaceutical methods.

For nicotinamide and related active substances, the active substance content in the finished dosage form is 1-5000 mg, such as 1-3000 mg, preferably 10-1000 mg, in the case of oral administration; the enemas and/or suppositories can contain an amount of 10 mg to 5000 mg of the active substance. Depending on the intensity and severity of the inflammatory disease, the dosage forms are administered once or several times daily or in another dosage regimen to be chosen by a physician. The daily dose of nicotinamide for an adult human is typically 50 mg-2 g, such as 50-200 mg or 500 mg-2 g.

For 5-ASA, the active substance content in the finished dosage form is 1-5000 mg, 1-3000 mg, preferably 10-1500 mg, in the case of oral administration; the enemas and/or suppositories can contain an amount of 10 mg to 5000 mg of the active substance. Depending on the intensity and severity of the inflammatory disease, the dosage forms are administered once or several times daily or in another dosage regimen to be chosen by a physician. The daily dose of 5-ASA for an adult human is typically 500 mg-5 g, such as 1-4.8 g.

As used herein, the terms "treatment", "treat", and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein, the terms "prophylaxis" and "prevent" refer to delaying the onset of or reducing the likelihood of developing a disease or disorder or one or more symptoms thereof, as compared to an untreated control population.

A further aspect of the invention described herein is the efficient use of the claimed medicaments on the basis of genetic and/or microbiological data and specific needs of the individuals to be treated. New insights into the genetic predisposition of individuals for all types of diseases (in particular also diseases where the interaction between intestinal microbiota and intestines is impaired) and into pharmacogenetics indicate that an evidence-based personalized medicine including genetic analyses of relevant risk genes and also of genes which code e.g., for cell surface receptors, transporter proteins, metabolism enzymes or signal transduction proteins, which interact with the medicament and/or its metabolites and/or its downstream effectors, can contribute information and improvements with respect to the type of use, the mode of application, the time(s) of use, the dose and/or the dosage regimen of the medicaments described herein. Individuals who may benefit from this personalized treatment include those with reduced serum tryptophan, altered expression of $B^0AT1$ (e.g., in intestinal epithelial cells) and $B^0AT1$ polymorphisms. This applies analogously to analyses of the intestinal microbiota, particularly when a stool sample indicates a change in the microbiota. The present invention thus also comprises the use of suitable genetic and/or microbiological test methods to identify individuals particularly susceptible to the medicaments according to the invention and/or to adapt the use of the medicaments according to the invention to the individual circumstances. This also comprises expressly the use of 5-ASA in combination with different substances (nicotinamide and/or related active substances) in different modes of administration depending on the genetic and microbiological properties of the individual. For these purposes, it is possible to use laboratory tests and/or suitable test kits and also measuring methods, devices and/or kits to be employed by a physician, user and/or patient, e.g., to take stool samples or to analyse suitable parameters in the blood, urine or other body fluids.

EXEMPLIFICATION

There are variable possibilities to advantageously develop, and develop further, the teaching of the present invention. For this purpose, reference is made to the examples below which describe the invention in a representative way.

Example 1

In order to characterise the combined effect of 5-ASA and nicotinamide (NAM) in controlled release formulations for targeted delivery of both substances to the intestinal epithelium, a study was conducted in a dextrane sodium sulfate (DSS) colitis model in mice. In this study, a controlled release granule formulation for was tested in two different doses (30 mg/kg and 60 mg/kg). As a representative controlled release formulation for 5-ASA, 5-ASA granules (PENTASA®; Ferring Pharmaceuticals, Saint-Prex, Switzerland) were used both alone and in combination with the NAM granules.

The controlled release formulation for NAM is a granulate of 25% nicotinamide, 70% dibasic calcium phosphate and 5% Povidone K30. The mean particle size was 234 µm. The granulate was subsequently film coated with Ethylcellulose 7 to achieve a 30% weight gain and a mean particle size of 640 µm. Filtering removed particles with a size of less than 355 µm. Control granules replaced NAM with an equivalent amount of dibasic calcium phosphate.

Male C57BL/6J mice (specific pathogen free; Charles River Laboratories, Saint-Germain-sur-l'Arbresle, France) were taken into the test facility at >12 weeks of age and acclimatised for 1 week. The diet during the acclimatisation phase was diet A4, produced by SAFE (Scientific Animal Food and Engineering, Augy, France). After the acclimatisation, the diet was changed to a custom-made diet without tryptophan or nicotinic acid or nicotinamide (Trp/Nia/NAM-free diet), which was manufactured by Ssniff (Soest, Germany). The Trp/Nia/NAM-free diet was supplied as a powder, which was used to prepare food pellets with either no granules (control), NAM granules, 5-ASA granules, or a combination of NAM and 5-ASA granules. Granules were homogeneously dispersed in the diet. Food pellets of approximately 2 cm length and 1 cm diameter were formed with a minimum amount of sterile water, frozen in single-use aliquots at −20° C. for storage and freshly thawed daily for feeding the mice. The granule content of the food pellets was defined as follows with a calculation basis of 30 g bodyweight and a daily food intake of 3 g.

5-ASA granules (target dose of 5-ASA: 150 mg/kg bodyweight; 5-ASA content: 52%): 4.5 mg 5-ASA needed in 3 g of food; 8.65 mg of granules needed in 3 g of food; 2.88 g of granules added per kg of food. The fixed doses for the other granules were calculated in an analogous fashion.

NAM granules (target doses of NAM: 30 or 60 mg/kg bodyweight; NAM content: 19.1%): for 30 mg/kg NAM, 1.57 g of granules per kg of food; for 60 mg/kg NAM, 3.14 g of granules per kg of food; for 120 mg/kg NAM, 6.28 g of granules per kg of food.

The Trp/Nia/NAM-free diet with or without granules were administered until termination of the mice. After 10 days of Trp/Nia/NAM-free diet, the mice were challenged with 1.5% DSS (TDB Consultancy, Uppsala, Sweden) in the drinking water for 5 days and terminated after another 3 days during which they were supplied with normal drinking water.

The treatment regimen was carried out with six groups of 15 mice each, which were treated as follows:

Group 1: control food.

Group 2: NAM granules in the diet (final dose: 30 mg/kg bodyweight).

Group 3: NAM granules in the diet (final dose: 60 mg/kg bodyweight).

Group 4: 5-ASA granules in the diet (final dose: 150 mg/kg bodyweight).

Group 5: NAM granules in the diet (final dose: 30 mg/kg bodyweight) plus 5-ASA granules in the diet (final dose: 150 mg/kg bodyweight).

Group 6: NAM granules in the diet (final dose: 60 mg/kg bodyweight) plus 5-ASA granules in the diet (final dose: 150 mg/kg bodyweight).

After termination, the evaluation of inflammation and colonic lesions at the histological level was performed according to Dieleman et al. 1998 (Clin. Exp. Immunol. 114:385). The score includes the following parameters: the severity of inflammation, its extension (percentage of involvement) and the presence of crypt damage throughout the colon.

Figure 1:
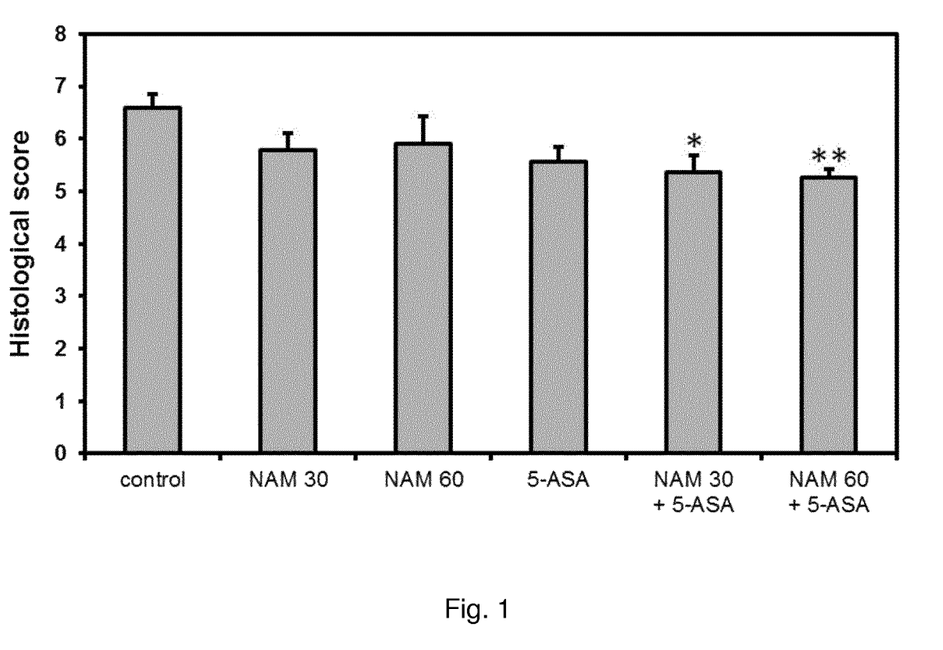

As shown in FIG. 1, the monotherapy with either NAM or 5-ASA granules only led to a trend towards histological improvement, whereas their combination led to a significant therapeutic effect (*, $p=0.04$ for 30 mg/kg NAM plus 5-ASA; **, $p=0.005$ for 60 mg/kg NAM plus 5-ASA), demonstrating a combined therapeutic effect of the two active substances in this rather harsh setting. It is surprising that the effect of the 5-ASA alone was improved upon, as the dose administered is the optimized dose for this DSS colitis model.

Example 2

In a second and much larger study, NAM and 5-ASA controlled release granules were used again in the murine DSS colitis model (see Example 1) to confirm the anti-inflammatory properties of NAM in one low dose (30 mg/kg) and to investigate two higher dosages (120 or 240 mg/kg) not administered in the first study.

In particular, this second study aimed to investigate potential synergistic anti-inflammatory properties of NAM combined with a suboptimal dose of 5-ASA granules (75 mg/kg instead of the optimal dose of 150 mg/kg).

One very important difference to the first study described in Example 1 was the fact that the mice received normal food with normal levels of tryptophan, nicotinic acid and nicotinamide (SAFE diet A4; Scientific Animal Food and Engineering, Augy, France; see Example 1). Therefore, any effects observed in this second study cannot be due to supplementation of NAM to NA/NAM/Trp-starved mice.

1. Materials and Methods 1.1. Test System and Experimental Design

In the present study, the same DSS colitis model in C57BL/6J mice as in Example 1 was used, albeit with some minor modifications: 2.5% DSS were used to provide a stronger DSS challenge. The animals were acclimatised for one week to stabilise their microbiota, randomised into 9 different groups as illustrated in the following Table 1 and then kept for 10 days on the different diets (days -10 to -1) before inducing colitis by DSS in the drinking water (day 0-day 6) followed by a washout period with normal drinking water (day 6-day 9). All groups received 2.5% DSS.

TABLE 1

| Groups (n = 15) | Treatment | Active compound(s) |
|---|---|---|
| 1 | DSS control (only reconstituted food) | none |
| 2 | 5-ASA granules in food (150 mg/kg) | 4.5 mg/day of 5-ASA |

TABLE 1-continued

| Groups (n = 15) | Treatment | Active compound(s) |
|---|---|---|
| 3 | 5-ASA granules in food (75 mg/kg) | 2.25 mg/day of 5-ASA |
| 4 | NAM granules in food (30 mg/kg) | 0.9 mg/day of NAM |
| 5 | NAM granules in food (120 mg/kg) | 3.6 mg/day of NAM |
| 6 | NAM granules in food (240 mg/kg) | 7.2 mg/day of NAM |
| 7 | NAM granules (30 mg/kg) + 5-ASA granules (75 mg/kg) in food | 0.9 mg/day of NAM + 2.25 mg/day of 5-ASA |
| 8 | NAM granules (120 mg/kg) + 5-ASA granules (75 mg/kg) in food | 3.6 mg/day of NAM + 2.25 mg/day of 5-ASA |
| 9 | NAM granules (240 mg/kg) + 5-ASA granules (75 mg/kg) in food | 7.2 mg/day of NAM + 2.25 mg/day of 5-ASA |

1.2. Specifications of Dosing, Food and Active Substances

TABLE 2

| | |
|---|---|
| Method and route | oral administration, active compounds mixed in food |
| Duration | daily from day −10 to day until day 9 (euthanasia) |
| Frequency | food ad libitum |
| Volume | dosages based on daily food consumption of mice and determined for a mouse weighing 30 g |

The 5-ASA granules were the same as in Example 1. Their 5-ASA content was 52% (one granule weighed 0.5 mg and contained 0.26 mg of 5-ASA). The 5-ASA granules were mixed with regular food for preparation of single-use food aliquots, which were stored frozen at −20° C. and thawed daily prior to feeding the mice. The food aliquots had a 5-ASA content of either 0.75 mg/g food or 1.5 mg/g food, resulting in a daily uptake of 2.25 mg or 4.5 mg 5-ASA (in 3 g of food) and doses of 75 or 150 mg/kg body weight of 5-ASA (for a 30-g mouse), respectively. To administer the desired doses of 5-ASA per day, the mice had to be dosed with the ~2-fold amount of 5-ASA granules with 52% 5-ASA content (i.e., a 5-ASA dose of 150 mg/kg body weight or 4.5 mg/mouse required a daily granule uptake of 288 mg/kg or 8.65 mg/mouse). Therefore, the food was prepared with 2.88 g of granules per kg of food (for the 150 mg/kg dose) or 1.44 g/kg (for the 75 mg/kg dose).

The NAM granules of the present example were produced by the same manufacturer and in a similar formulation (diameter: 0.355-0.500 mm; NAM content: 19.1%) as in Example 1. Three kinds of food were prepared in an analogous fashion to the food with 5-ASA granules as described above. To administer the desired doses of NAM per day, the mice had to be dosed with the ~5-fold amount of granules with 19.1% NAM content (e.g., a NAM dose of 30 mg/kg body weight or 0.9 mg/mouse of NAM required a daily granule uptake of 157 mg/kg or 4.71 mg/mouse). Therefore, the food preparation for the three dose groups was performed as follows: 1.57 g of granules per kg of food for the 30 mg/kg dose group, 6.28 g of granules per kg of food for the 120 mg/kg dose group and 12.56 g of granules per kg of food for the 240 mg/kg dose group.

For the control group, food without granules was processed in the same fashion as the granule-containing food preparations described above in order to exclude preparation artefacts.

1.3. Analysis and Scoring of Disease Activity Index Parameters

After euthanasia, the colon was analysed and the disease activity index (DAI; score 0-9) was scored using an adapted DAI system based on Melgar et al. 2005 (Am. J. Physiol. Gastrointest. Liver Physiol. 288:G1328). As no visible blood was observed, the blood scoring parameter according to Melgar et al. was changed to scoring the signal strength for occult blood in feces detected by the ColoScreen test (Helena Laboratories, Beaumont, Tex., USA). This signal strength scoring was performed independently by two investigators blinded to the identity of the samples.

TABLE 3

| Score | Inflammatory score | Diarrhea score | Occult fecal blood |
|---|---|---|---|
| 0 | Normal | Normal pellets | None |
| 1 | Slight inflammation | Slightly loose feces | Weak signal |
| 2 | Moderate inflammation and/or edema | Loose feces | Medium signal |
| 3 | Heavy inflammation and/or ulcerations and/or edema | Watery diarrhea | Strong signal |

1.4. Statistical Analysis

All comparisons were analysed using the Anova Test for two independent samples in the StatXact software (Cytel, Cambridge, Mass., USA). Differences were considered statistically significant if the p value was <0.05.

2. Results and Conclusions

No mortality was recorded.

The dose group with 150 mg/kg 5-ASA represents the optimal treatment in this model according to the prior art and served as a reference treatment group.

Figure 2:
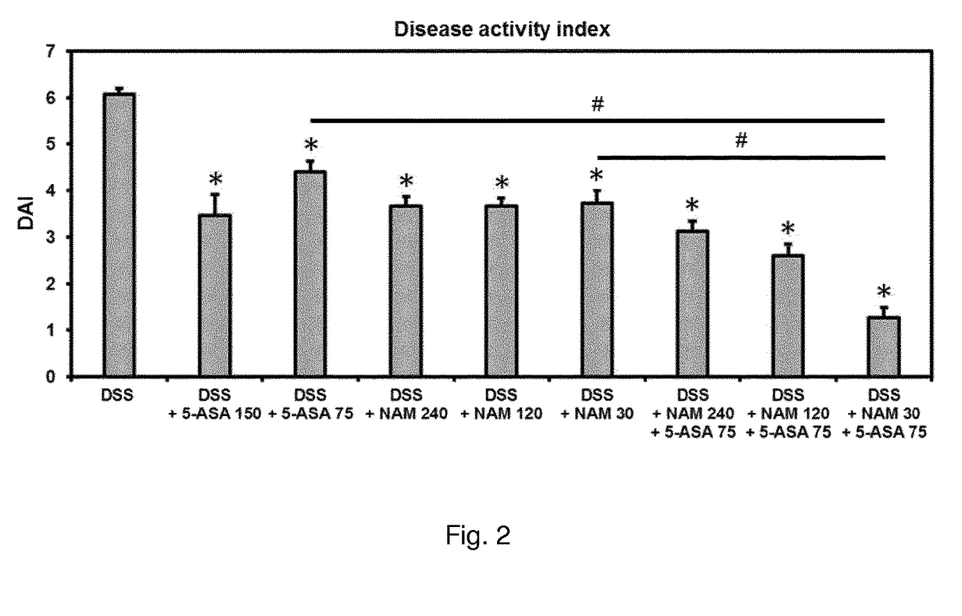
FIG. 2 shows the disease activity index (DAI) combined from results of macroscopic scoring of inflammation, stool consistency (diarrhea) and the presence of occult blood in the feces of dextrane sodium sulfate (DSS)-challenged mice on a normal diet supplemented with different doses and combinations of controlled release granules containing NAM or 5-ASA. *, p<0.0001 vs. control (DSS); # p<0.0001 vs. the indicated baseline.

As shown in FIG. 2, the disease activity index was highly significantly ($p<0.0001$) reduced by all treatments. Interestingly, doubling the dose of 5-ASA from 75 to 150 mg/kg led to a stronger decrease of the DAI, whereas NAM treatment showed no dose response in the DAI from 30 to 240 mg/kg. This was in good agreement with the findings from the first study described in Example 1. However, different doses of NAM in combination with the suboptimal 75 mg/kg dose of 5-ASA consistently and across all parameters (FIG. 3) showed an inverse dose effect with highly significant differences of the optimal combination of 30 mg/kg NAM and 75 mg/kg 5-ASA compared to the baselines of 30 mg/kg NAM alone or 75 mg/kg 5-ASA alone. This indicates a true synergistic mechanism of previously unknown efficacy beyond merely additive effects. In the following Table 4, the percentaged improvements of the DAI compared to the control group are summarised.

TABLE 4

| | % improvement of DAI vs DSS |
|---|---|
| 150 mg/kg 5-ASA | 43 |
| 75 mg/kg 5-ASA | 28 |
| 240 mg/kg NAM | 40 |
| 120 mg/kg NAM | 40 |
| 30 mg/kg NAM | 39 |
| 240 mg/kg NAM + 75 mg/kg 5-ASA | 49 |
| 120 mg/kg NAM + 75 mg/kg 5-ASA | 57 |
| 30 mg/kg NAM + 75 mg/kg 5-ASA | 79 |

Table 5 lists the p values of the most efficacious combination treatment (30 mg/kg NAM and 75 mg/kg 5-ASA; abbreviated NAM 30+5-ASA 75) versus the baselines of the control group (DSS), 30 mg/kg NAM alone (NAM 30), 75 mg/kg 5-ASA alone (5-ASA 75) or 150 mg/kg 5-ASA alone (5-ASA 150, as the state-of-the-art reference treatment).

TABLE 5

| p values | NAM 30 + 5-ASA 75 vs. DSS | NAM 30 + 5-ASA 75 vs. NAM 30 | NAM 30 + 5-ASA 75 vs. 5-ASA 75 | NAM 30 + 5-ASA 75 vs. 5-ASA 150 |
|---|---|---|---|---|
| DAI | <0.0001 | <0.0001 | <0.0001 | <0.0001 |
| Inflammation | <0.0001 | 0.049 | 0.00041 | 0.00041 |
| Diarrhea | <0.0001 | <0.0001 | <0.0001 | <0.0001 |
| Occult blood | <0.0001 | 0.01 | 0.01 | not significant |

Figure 3:
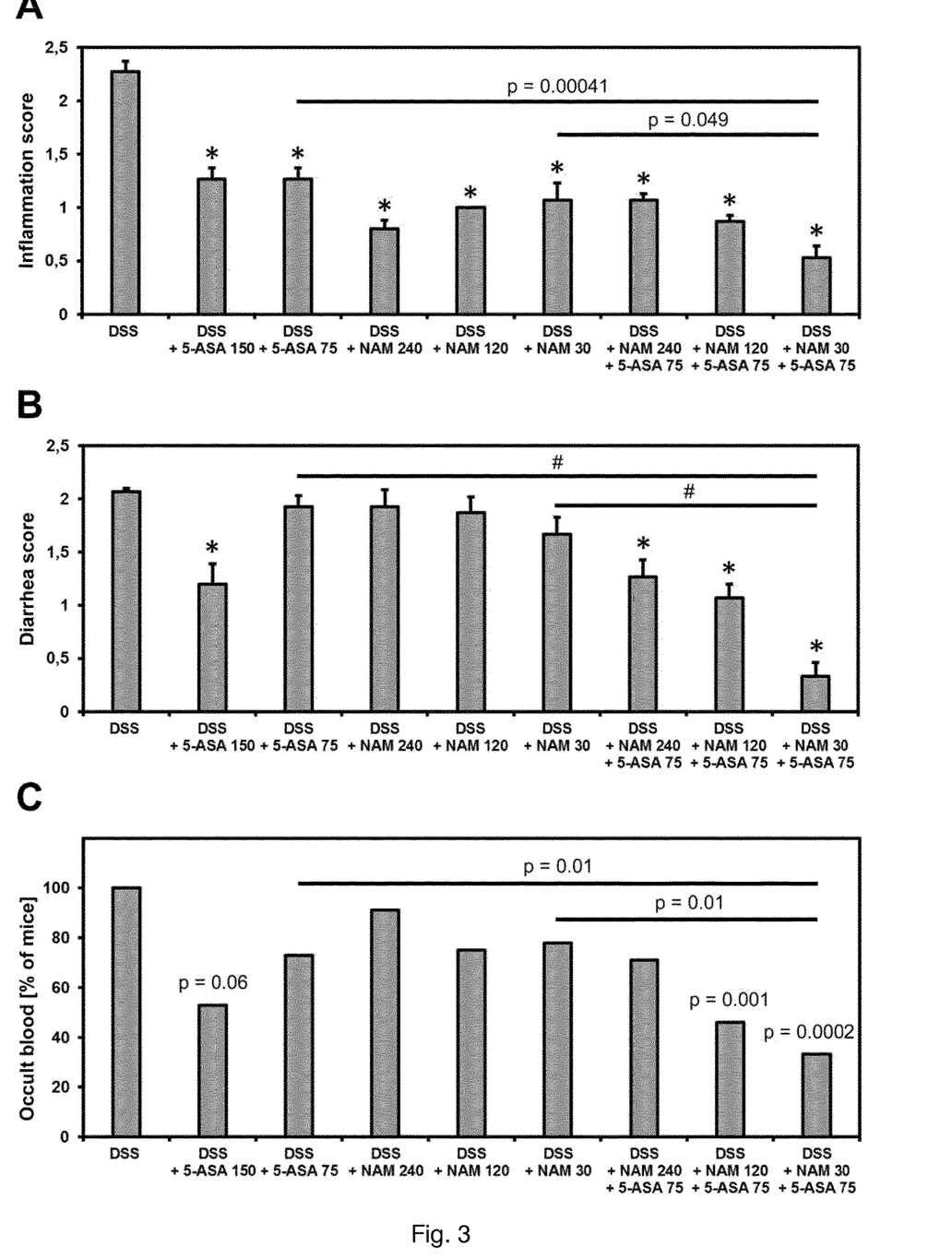
FIG. 3 shows the results of the individual parameters of the disease activity index (DAI) data presented in FIG. 2, namely the macroscopic scoring of inflammation (A), stool consistency (diarrhea) (B) and the presence of occult blood in the feces (C). *, p<0.0001 vs. control (DSS); # p<0.0001 vs. the indicated baseline.

The highly significant reduction of the DAI was based on the following three important parameters for judging intestinal inflammation:

1. The macroscopic inflammation score representing the presence and amount of inflammation, ulceration and/or edema showed that all treatments more or less strongly and highly significantly ($p<0.0001$) reduced DSS-induced inflammation (FIG. 3A). Here, a slight dose-dependent effect of NAM was observed, whereas the two 5-ASA doses showed no difference. As with the other parameters, a significant, synergistic improvement of the optimal combination of 30 mg/kg NAM and 75 mg/kg 5-ASA compared to all baselines was detected (FIG. 3A; Table 5).

2. The stool consistency (diarrhea) was hardly improved by the different NAM doses or the 75 mg/kg 5-ASA dose alone, only the optimal treatment with 150 mg/kg 5-ASA showed a significant effect (FIG. 3B). In contrast, the different combinations of NAM and 75 mg/kg 5-ASA showed significant and inversely dose-dependent effects, culminating in the highly significant, synergistic superiority of the optimal combination of 30 mg/kg NAM and 75 mg/kg 5-ASA compared to all baselines (FIG. 3B; Table 5). In this group, mice even had normal stools.

3. On the day of necropsy, the presence of blood in feces was analysed for each mouse. As no visible blood was observed, the presence of occult blood was measured. In the control DSS group, occult blood was found in the feces of all mice (FIG. 3C). As expected, a strong and significant effect was observed with 5-ASA administered at its optimal dosage of 150 mg/kg compared to control mice (53% vs. 100% of mice having blood in the feces). Similar to the other parameters tested for DAI scoring, a significant, synergistic improvement of the optimal combination of 30 mg/kg NAM and 75 mg/kg 5-ASA compared to all baselines except for the highly efficacious 150 mg/kg 5-ASA was measured (FIG. 3C; Table 5).

Taken together, the protective efficacy of NAM at a low dose (30 mg/kg) observed in the first study (Example 1) was confirmed, and the combination of a clearly suboptimal dose of 5-ASA (75 mg/kg) with different doses of NAM led to a highly significant, even dramatic, synergistic improvement over all relevant baselines. As the dose-relationship with NAM was inverse, the observed synergy is not due to additive dose effects, but a surprising synergy in the most significant sense. Moreover, the fact that the formulations and combinations of the present invention are active even with normal levels of tryptophan and/or NA and/or NAM in the food (cf. Example 1) clearly indicates that the protective efficacy of NAM and/or combinations of NAM and 5-ASA is not only due to supplementation of NAM in the diet.

The examples above serve to explain the invention, but are not intended to limit the scope.

The invention claimed is:

1. A pharmaceutical product for beneficially influencing the intestinal microbiota, comprising as separate compounds:
   (i) 10-3000 mg 5-aminosalicylic acid or a prodrug thereof formulated for oral administration and comprising one or more of
      (a) a coating for controlled and/or delayed release, wherein the coating is resistant to gastric juice and dissolves depending on the pH,
      (b) a matrix for controlled and/or delayed release, and
      (c) a carrier for controlled and/or delayed release; and
   (ii) 10-3000 mg nicotinamide (NAM) formulated for oral administration and formulated to selectively release the NAM in the lower small intestine, the colon, or both, for topical efficacy where the intestinal microbiota to be influenced are located, for beneficially influencing the intestinal microbiota, wherein the NAM comprises one or more of
      (a') a coating for controlled and/or delayed release, wherein the coating is resistant to gastric juice and dissolves depending on the pH,
      (b') a matrix for controlled and/or delayed release, and
      (c') a carrier for controlled and/or delayed release.

2. The product of claim 1, wherein (i) and (ii) are formulated in separate dosage forms.

3. The product of claim 1, wherein (i) and (ii) are formulated in the same dosage form, and optionally are physically segregated in the same dosage form.

4. The product of claim 1, comprising a composition comprising both (i) and (ii).

5. The product of claim 4, wherein the composition is formulated to selectively release (i) and (ii) in the lower small intestine, the colon, or both, for topical efficacy.

6. The product of claim 4, wherein (i) is 10-3000 mg 5-aminosalicylic acid formulated for oral administration and comprising one or more of
   (a) a coating for controlled and/or delayed release, wherein the coating is resistant to gastric juice and dissolves depending on the pH,
   (b) a matrix for controlled and/or delayed release, and
   (c) a carrier for controlled and/or delayed release;
wherein the composition is formulated to selectively release (i) and (ii) in the lower small intestine, the colon, or both, for topical efficacy where the intestinal microbiota to be influenced are located.

7. The product of claim 4, wherein the composition is formulated for oral administration and is formulated to selectively release (i) and (ii) for specific local effect in the lower small intestine, the colon, or both, where the intestinal microbiota to be influenced are located.

8. The product of claim 4, wherein the composition is formulated for oral administration and to provide delayed release of (i) and (ii) for specific local effect in the lower small intestine, the colon, or both, where the intestinal microbiota to be influenced are located.

9. The product of claim 4, wherein the composition is formulated for oral administration and to provide controlled release of (i) and (ii) for specific local effect in the lower small intestine, the colon, or both, where the intestinal microbiota to be influenced are located.

10. The product of claim 7, wherein the composition is formulated in a finished oral dosage form comprising 10-1500 mg 5-aminosalicylic acid and 10-1000 mg nicotinamide per finished dosage form.

11. The product of claim 1, wherein (i) and (ii) are physically segregated in the same dosage form.

12. The product of claim 1, wherein (a) and (a') independently are a film coating comprising an acrylic polymer, a methacrylic polymer, or a mixture thereof.

13. The product of claim 1, wherein (a) and (a') independently comprise a coating agent, the coating agent comprising a water-insoluble wax, a polyacrylate, a polymethacrylate, or a mixture of any two or more thereof.

14. The product of claim 1, wherein (a) and (a') independently comprise a water-insoluble cellulose.

* * * * *